US009302113B2

(12) United States Patent  
Ranu et al.

(10) Patent No.: US 9,302,113 B2
(45) Date of Patent: Apr. 5, 2016

(54) SYSTEMS AND METHODS FOR IDENTIFYING ANODE PLACEMENT BASED ON CEREBROSPINAL FLUID THICKNESS

(71) Applicant: BOSTON SCIENTIFIC NEUROMODULATION CORPORATION, Valencia, CA (US)

(72) Inventors: Emarit A. S. Ranu, Fort Collins, CO (US); Dongchul Lee, Agua Dulce, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/338,306

(22) Filed: Jul. 22, 2014

(65) Prior Publication Data

US 2015/0032187 A1    Jan. 29, 2015

Related U.S. Application Data

(60) Provisional application No. 61/859,569, filed on Jul. 29, 2013.

(51) Int. Cl.
*A61N 1/36* (2006.01)
*A61N 1/05* (2006.01)

(52) U.S. Cl.
CPC .......... *A61N 1/36185* (2013.01); *A61N 1/0553* (2013.01); *A61N 1/36139* (2013.01)

(58) Field of Classification Search
CPC . A61N 1/0551; A61N 1/0553; A61N 1/3605; A61N 1/36135; A61N 1/36185
USPC .......................................... 607/62, 115–117
See application file for complete search history.

(56) References Cited

U.S. PATENT DOCUMENTS

| 6,181,969 | B1 | 1/2001 | Gord |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 7,244,150 | B1 | 7/2007 | Brase et al. |
| 7,437,193 | B2 | 10/2008 | Parramon et al. |
| 7,450,997 | B1 | 11/2008 | Pianca et al. |
| 7,672,734 | B2 | 3/2010 | Anderson et al. |
| 7,761,165 | B1 | 7/2010 | He et al. |
| 7,783,359 | B2 | 8/2010 | Meadows |

(Continued)

OTHER PUBLICATIONS

Holsheimer, J. et al. "MR Assessment of the Normal Position of the Spinal Cord in the Spinal Canal." AJNR 15:951-959. 1994.*

(Continued)

*Primary Examiner* — Allen Porter, Jr.
(74) *Attorney, Agent, or Firm* — Lowe Graham Jones PLLC; Bruce E. Black

(57) ABSTRACT

A method of stimulating a portion of a spinal cord of a patient includes identifying an arrangement of electrodes including a relative placement of each electrode within the arrangement; identifying a vertebral level for implantation of the arrangement and a position of the arrangement with respect to the spinal cord; determining by calculation, for a selection of at least one cathode from the electrodes, at least two anode guard electrodes from the electrodes including in the calculation an estimated thickness of cerebrospinal fluid at the vertebral level; and stimulating the portion of the spinal cord of the patient at the vertebral level using the at least one cathode and the at least two anode guard electrodes.

19 Claims, 9 Drawing Sheets

(56) References Cited

U.S. PATENT DOCUMENTS

| | | |
|---|---|---|
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 2007/0150036 A1 | 6/2007 | Anderson |
| 2009/0187222 A1 | 7/2009 | Barker |
| 2009/0276021 A1 | 11/2009 | Meadows |
| 2010/0057163 A1* | 3/2010 | Moffitt et al. ............ 607/46 |
| 2010/0076535 A1 | 3/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0014580 A1* | 1/2012 | Blum et al. ............ 382/131 |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |

OTHER PUBLICATIONS

Dynamics of the Cerebrospinal Fluid and the Spinal Dura Matter, A. N. Martins, J. K. Wiley and P. W. Myers, J Neurol Neurosurg Psychiatry 1972 35: 468-473.

Cerebrospinal Fluid Pulsation Amplitude and Its Quantitative Relationship to Cerebral Blood Flow Pulsations: a Phase-Contrast MR Flow Imaging Study, R. A. Bhadelia, A. R. Bogdan, R. F. Kaplan and S. M. Wolpert, Neuroradiology 1997 39: 258-264.

Influence of Systemic and Cerebral Vascular Factors on the Cerebrospinal Fluid Pulse Waves, J. Hamer, E. Alberti, S. Hoyer and K. Wiedemann, J. Neurosurg. 1977 46: 36-45.

From Cerebrospinal Fluid Pulsation to Noninvasive Intracranial Compliance and Pressure measured by MRI Flow Studies, N. Alperin, M. Mazda, T. Lichtor and S. H. Lee, Current Medical Imaging Reviews 2006 2: 117-129.

* cited by examiner

SYSTEMS AND METHODS FOR IDENTIFYING ANODE PLACEMENT BASED ON CEREBROSPINAL FLUID THICKNESS

CROSS-REFERENCE TO RELATED APPLICATIONS

This application claims the benefit under 35 U.S.C. §119 (e) of U.S. Provisional Patent Application Ser. No. 61/859,569, filed Jul. 29, 2013, which is incorporated herein by reference.

FIELD

The present invention is directed to the area of implantable electrical stimulation systems and methods of making and using the systems. The present invention is also directed methods and systems for identifying anode guard electrodes for use with cathode electrodes, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated and, in particular, the stimulator can be implanted near the spinal cord (for example, in the epidural space) for stimulation of the spinal cord. The pulse generator in the control module generates electrical pulses that are delivered by the electrodes to body tissue.

BRIEF SUMMARY

One embodiment is a method of stimulating a portion of a spinal cord of a patient. The method includes identifying an arrangement of electrodes including a relative placement of each electrode within the arrangement; identifying a vertebral level for implantation of the arrangement and a position of the arrangement with respect to the spinal cord; determining by calculation, for a selection of at least one cathode from the electrodes, at least two anode guard electrodes from the electrodes including in the calculation an estimated thickness of cerebrospinal fluid at the vertebral level; and stimulating the portion of the spinal cord of the patient at the vertebral level using the at least one cathode and the at least two anode guard electrodes.

Another embodiment is a method of identifying a selection of electrodes for stimulating a portion of a spinal cord of a patient. The method includes identifying an arrangement of electrodes including a relative placement of each electrode within the arrangement; identifying a vertebral level for implantation of the arrangement and a position of the arrangement with respect to the spinal cord; determining by calculation, for a selection of at least one cathode from the electrodes, at least two anode guard electrodes from the electrodes including in the calculation an estimated thickness of cerebrospinal fluid at the vertebral level; and displaying an indication of the at least two anode guard electrodes for view by a practitioner.

Yet another embodiment is a non-transitory computer-readable storage medium having processor-executable instructions. The processor-executable instructions when installed onto a system enable the system to perform actions, including receiving an indication of an arrangement of electrodes including a relative placement of each electrode within the arrangement; receiving a vertebral level for implantation of the arrangement and a position of the arrangement with respect to the spinal cord; determining by calculation, for a selection of at least one cathode from the electrodes, at least two anode guard electrodes from the electrodes including in the calculation an estimated thickness of cerebrospinal fluid at the vertebral level; and displaying an indication of the at least two anode guard electrodes.

A further embodiment is a system for determining electrodes for use in electrical stimulation. The system includes a display and at least one processor coupled to the display. The at least one processor is configured and arranged to receive an indication of an arrangement of electrodes including a relative placement of each electrode within the arrangement; receive a vertebral level for implantation of the arrangement and a position of the arrangement with respect to the spinal cord; determine by calculation, for a selection of at least one cathode from the electrodes, at least two anode guard electrodes from the electrodes including in the calculation an estimated thickness of cerebrospinal fluid at the vertebral level; and display on the display an indication of the at least two anode guard electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed methods and systems for identifying anode guard electrodes for use with cathode electrodes, as well as methods of making and using the leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads and paddle leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783.359; 7,792,590; 7,809,446; 7,949,395; 7,974,706; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615, all of which are incorporated by reference.

Figure 1:
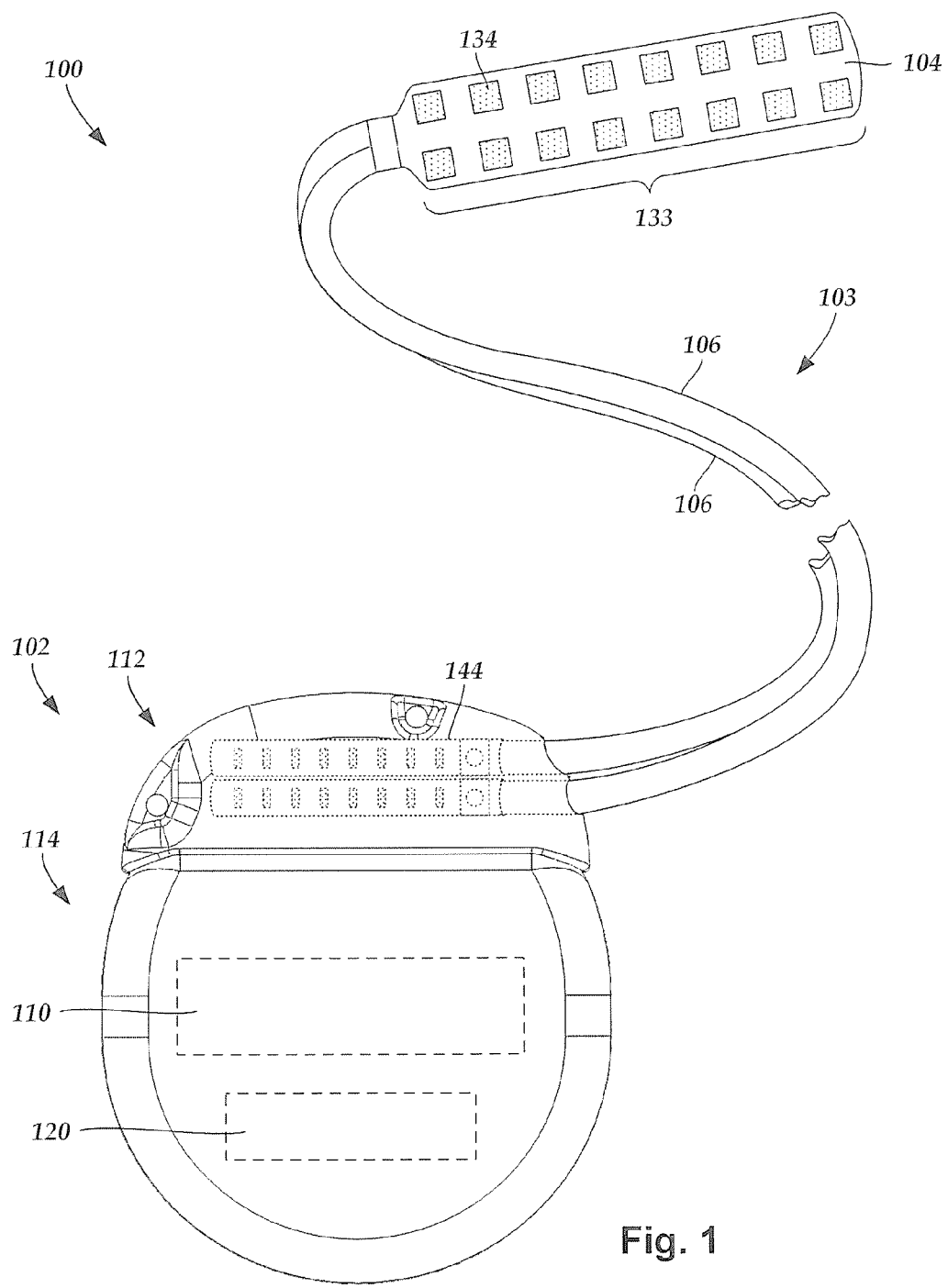
FIG. 1 is a schematic view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices. For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the paddle body including, for example, four, five, six, seven, eight, nine, ten, eleven, twelve, fourteen, sixteen, twenty-four, thirty-two, or more electrodes 134. The electrodes 134 can be disposed on the paddle body 104 in any suitable arrangement. In FIG. 1, the electrodes 134 are arranged into two columns, where each column has eight electrodes 134.

The electrodes of the paddle body 104 are typically disposed in, or separated by, a non-conductive, biocompatible material such as, for example, silicone, polyurethane, polyetheretherketone ("PEEK"), epoxy, and the like or combinations thereof. The paddle body 104 and the one or more lead bodies 106 may be formed in the desired shape by any process including, for example, molding (including injection molding), casting, and the like. The non-conductive material typically extends from the paddle body 104 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Figure 2A:
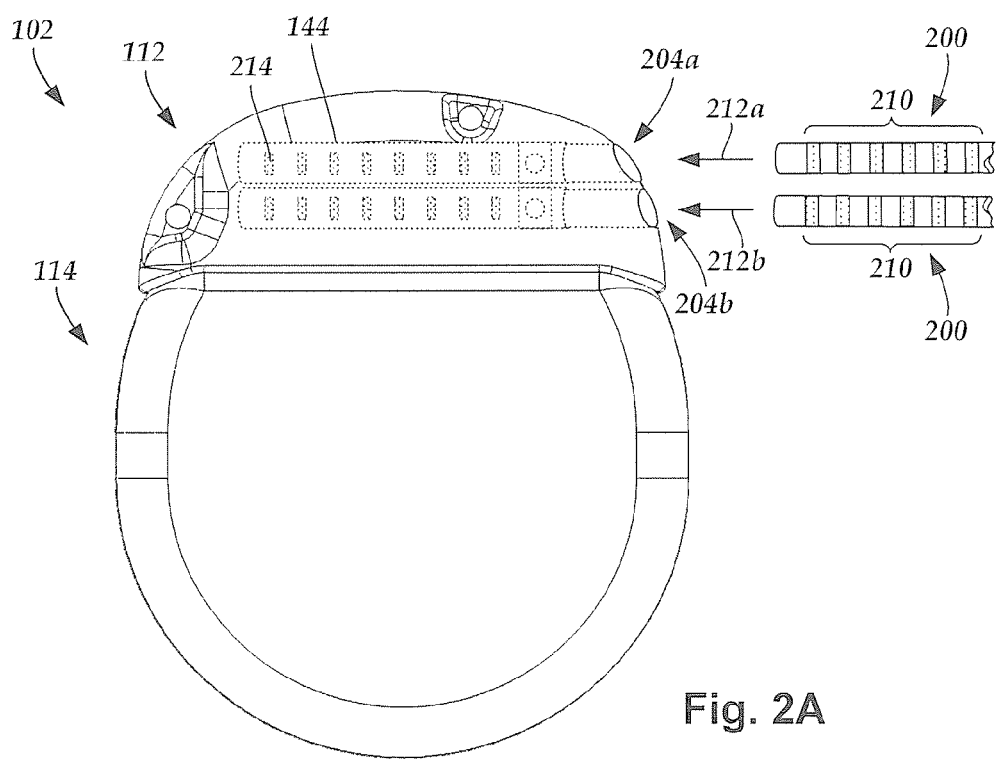
FIG. 2A is a schematic view of one embodiment of the control module of FIG. 1 configured and arranged to electrically couple to an elongated device, according to the invention.
Figure 2B:
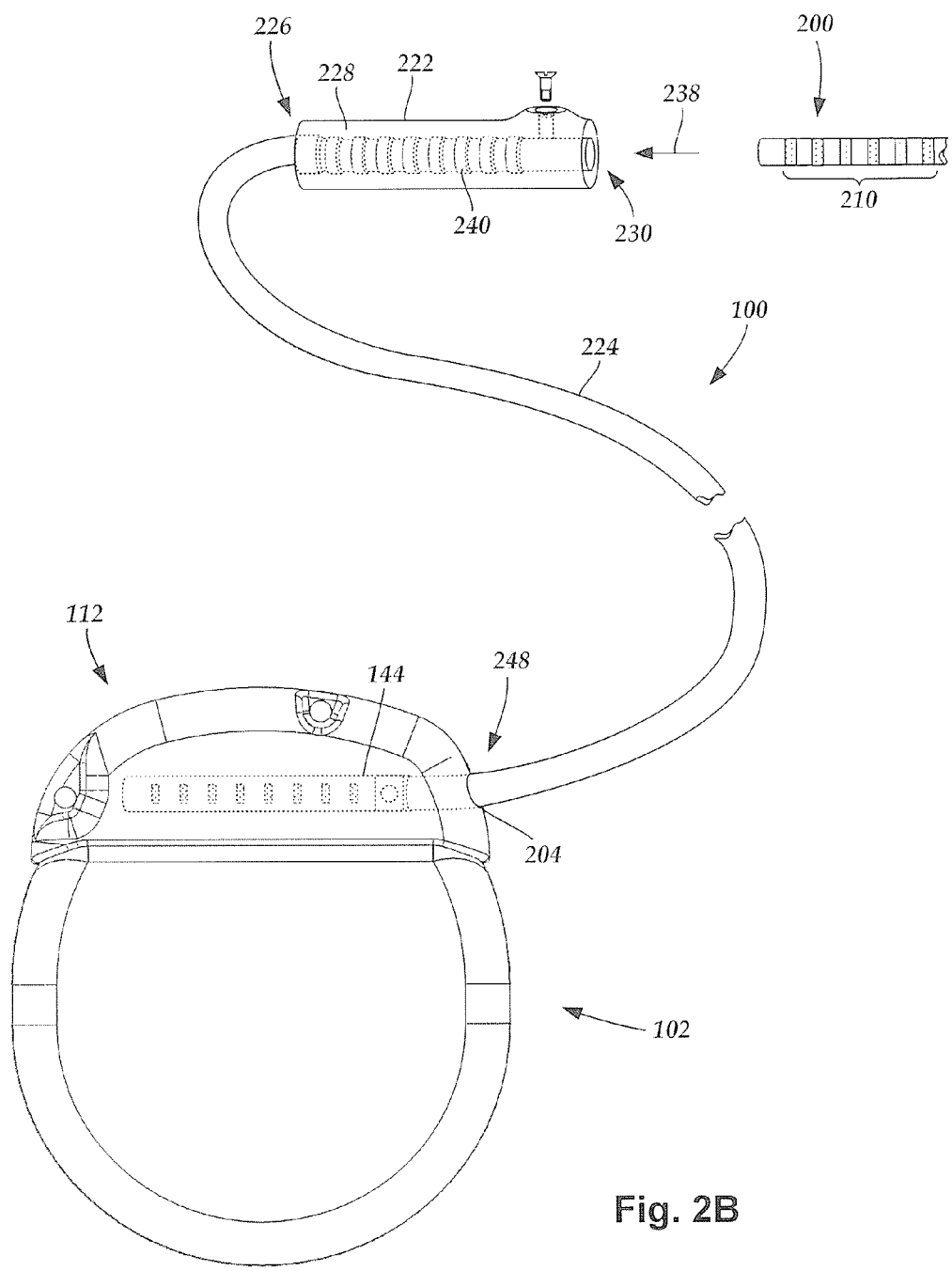
FIG. 2B is a schematic view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B). The connector contacts are disposed in connectors (e.g., 144 in FIGS. 1-2B; and 222 FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, one or more of the lead bodies 106 of FIG. 1, one or more intermediate devices (e.g., a splitter, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., one of the lead bodies 106 of FIG. 1, a splitter, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144 (e.g., the ports 204a and 204b of FIG. 1), or to receive multiple elongated devices 200 (e.g., both of the lead bodies 106 of FIG. 1), or both.

A lead extension connector 222 is disposed on the lead extension 224. In FIG. 2B the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Figure 3:
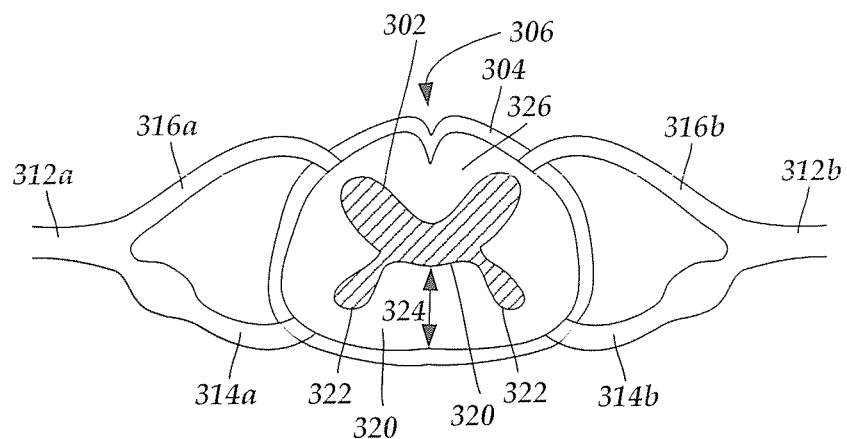
FIG. 3 is a schematic cross-sectional view of a portion of a spinal cord.

FIG. 3 schematically illustrates a transverse cross-sectional view of a spinal cord 302 surrounded by dura 304. The spinal cord 302 includes a midline 306 and a plurality of levels from which spinal nerves 312a and 312b extend. In FIG. 3A, the spinal nerves 312a and 312b are shown attaching to the spinal cord 302 at a particular spinal cord level via corresponding dorsal roots 314a and 314b and ventral (or anterior) roots 316a and 316b. Typically, the dorsal roots 314a and 314b relay sensory information into the spinal cord 302 and the ventral roots 316a and 316b relay motor information outward from the spinal cord 302. The spinal cord 302, as illustrated in FIG. 3, also includes the dorsal (or posterior) column 320 and the dorsal (or posterior) horns 322. Electrical stimulation leads are often implanted in the epidural space to stimulate the dorsal column or other regions of the spinal cord.

Cerebrospinal fluid 326 surrounds the spinal cord 302. Double-arrow 324 indicates the thickness (dCSF) of the cerebrospinal fluid within the spinal cord as measured between the dorsal column 320 and the dura 304. It will be understood that other measurements of the dCSF using different spinal cord features can also be used, but these measurements should be consistent with respect to the measurement definition. In adult humans, the dCSF is typically in the range of 1 to 10 mm and usually in the range of 1.5 to 8.5 mm. The dCSF varies along the length of the spinal cord and can vary by as much as a factor of three, four, or five between the smallest and largest dCSF values for an individual.

It at least some electrical stimulation systems, the electrodes of a stimulation lead are implanted in the epidural space and are often directed to stimulation of the dorsal column or dorsal horns (or both the dorsal column and dorsal horns) of the spinal cord. It has been found, however, that the cerebrospinal fluid can shunt the electrical stimulation current to the dorsal roots. Stimulation of the dorsal roots can result in uncomfortable sensations in the patient and is often an undesirable effect. It is also found that the thicker the cerebrospinal fluid, the more shunting occurs. The shunting of the stimulation current to the dorsal roots can result in a need to reduce the stimulation current amplitude range for to reduce unwanted or uncomfortable stimulation of the dorsal roots. This can reduce or restrict the available range of therapeutically effective stimulation current.

Electrical stimulation is often performed by selecting one or more electrodes, near the tissue to be stimulated, as cathodes. Cathodic stimulation current can be particularly therapeutically effective. In order to reduce the shunting effect, one or more electrodes that are mediolateral (e.g., transverse) or rostrocaudal (e.g., longitudinal) or both to the cathodic electrode(s) can be used as anode guard electrodes to steer the stimulation current away from the dorsal roots. When the lead is placed in a region (for example, the T5 vertebral level) where the cerebrospinal fluid thickness ("dCSF") is larger, the anode guards should be positioned relatively close to the stimulating cathode. When the dCSF is smaller (for example, the T11 vertebral level), the anode guards can be positioned further from the cathodes. In at least some embodiments, this can result in an increase of the available range of therapeutic current relative to an arrangement with the anodes closer at the same, smaller dCSF level.

Figure 14:
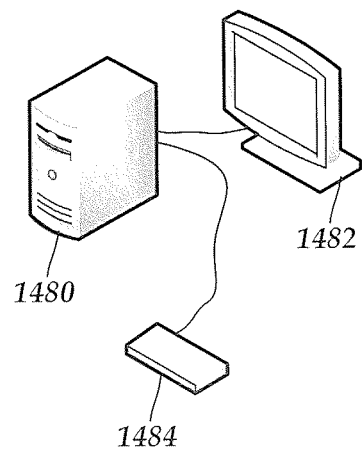
FIG. 14 is a schematic overview of one embodiment of a system on which the selection of anode guard electrodes can be performed, according to the invention.
Figure 4:
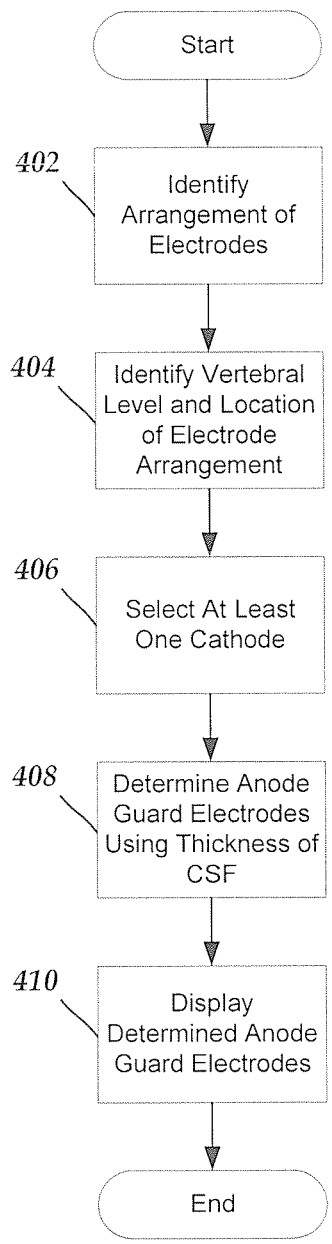
FIG. 4 is a schematic flowchart for one embodiment of a method of selecting anode guard electrodes, according to the invention.
Figure 5:
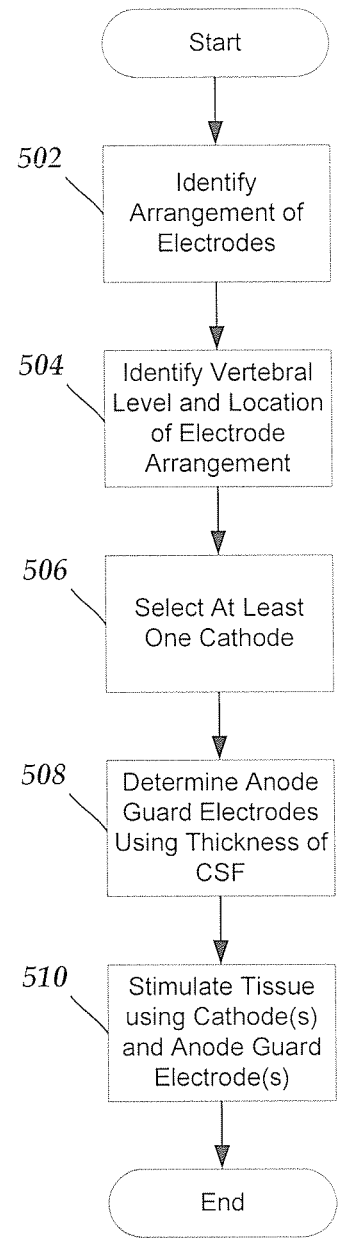
FIG. 5 is a schematic flowchart for one embodiment of another method of selecting anode guard electrodes, according to the invention.
Figure 13:
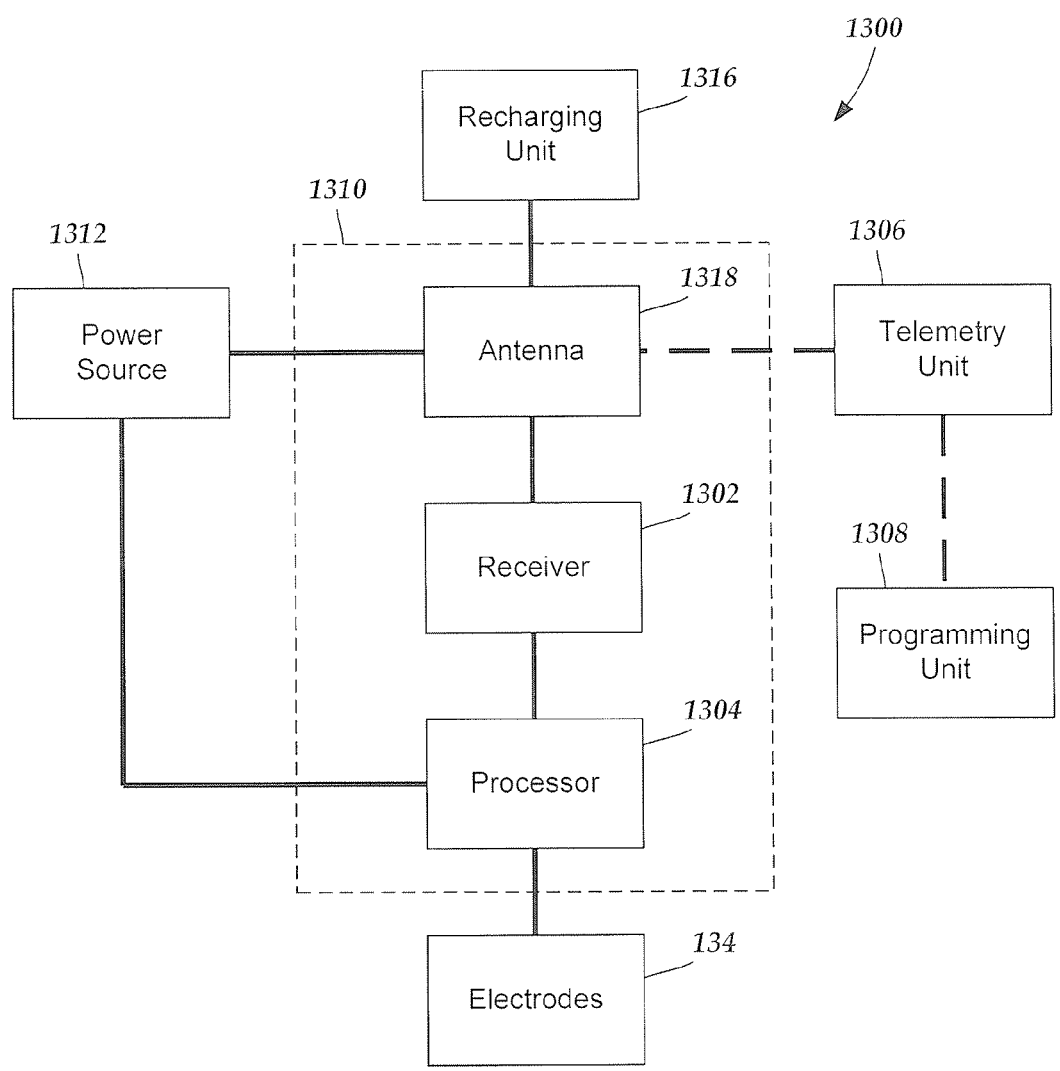
FIG. 13 is a schematic overview of one embodiment of components of a stimulation system, including an electronic subassembly disposed within a control module, according to the invention.

FIGS. 4 and 5 include flow charts of methods for stimulating a portion of the spinal cord that incorporate choosing the anode guards based, in part, on the cerebrospinal fluid thickness at the site of implantation. It will be understood that each block of the flowchart illustrations, and any combination of blocks in the flowchart illustrations, can be implemented by computer program instructions as software, or as hardware, or as any combination of software and hardware. These program instructions may be provided to a processor to produce a machine, such that the instructions, which execute on the processor, create means for implementing the actions specified in the flowchart block or blocks or described for the devices, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention. The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device. FIG. 14 illustrates one embodiment of an arrangement for performing these computer program instructions including a computer 1480 (which includes at least one processor), a display 1482, and an input device 1482 (such as a keyboard, mouse, touch screen, and the like). It will be understood, however, that some or all of the computer program instructions can be performed by devices other than computer, such as a control module, as described above, or an external device (see. FIG. 13 and the associated discussion below).

In the method illustrated in FIG. 4, the arrangement of the electrodes in the implanted lead or leads (see, examples of suitable leads in FIGS. 1-2B and 6-12 and the associated text) is identified (step 402). For example, the arrangement of the electrodes can be input into a processor by a user. The user might identify each electrode and its position and distance relative to one or more other electrodes. When multiple leads are used for stimulation, the user might identify each lead and its position and distance relative to other implanted leads. Alternatively or additionally, the user might input an identification code for a lead and the processor can obtain the electrode arrangement for that lead from an internal or external database.

The vertebral level (or range of levels) and location of the electrode arrangement relative to the spinal cord is also identified (step 404). For example, this information can also be input into the processor. The location of the electrode arrangement can be provided at any desired level of precision. In at least some embodiments, the vertebral level and location of the electrode arrangement can be the same information.

The user selects one or more electrodes of the electrode arrangement to act as a cathode (step 406). In some embodiments, the identity of the cathode(s) may change over time. For example, the stimulation regimen may include stimulation using different cathode(s) in a regular or irregular pattern. In some embodiments, the process may permit entry of the pattern of cathode(s) and the subsequent calculation, discussed below, will be performed, and results reported, for each selected cathode(s). In some embodiments, the user will input each cathode selection sequentially and the calculation, and reporting of results, will be performed before input of the next cathode selection. The user can select a specific electrode or electrodes as the cathode(s) or the user can select a particular stimulation site (e.g., a vertebral level or portion of a vertebral level), in which case the processor determines which electrode(s) of the electrode arrangement should act as cathode(s).

One or more anode guard electrodes are then determined using at least the position of the cathode(s) and an estimated cerebrospinal fluid thickness (based on the vertebral level identified) (step 408). In at least some embodiments, this determination is made by calculation using a processor. The processor could be, for example, in the control module (e.g., the processor 1304 of control module 1310 of FIG. 13) or in an external control module or in a separate device such as a laptop or desktop computer (e.g., computer 1480 of FIG. 14).

The estimated cerebrospinal fluid thickness (dCSF) could be a value measured for the patient in which the lead is to be implanted. More likely, however, the estimated cerebrospinal fluid distance is an average thickness (or at least a thickness value that is determined to be sufficiently representative of the actual value) for a group of individuals that may be published or otherwise obtained. For examples, values can be obtained from Holsheimer, et al., AJNR15:951-959 (1994), incorporated herein by reference. This thickness value may, for example, be a value used for all patients or may be selected based on one or more criteria such as, for example, age, gender, height, and the like.

Alternatively or additionally, the determination of the anode guard electrodes is based on a pre-determined maximum cathode/anode distance for the vertebral level that is selected. This pre-determined maximum cathode/anode distance is based, at least in part, on the cerebrospinal fluid thickness at the vertebral level.

In some embodiments, the user may also specify whether the anode guard electrodes will be positioned rostrocaudally (i.e., longitudinally relative to the spinal cord) or mediolaterally (i.e., transverse to the spinal cord) or both or any combination thereof. In some embodiments, anode guard electrodes for both positions can be determined.

The determined anode guard electrodes are then displayed for selection by a user or practitioner (step 410). For example, the processor that determines the anode guard electrodes can then provide an output to a display indicating one or more suggested anode guard electrodes. The display could be graphical or textual or any combination thereof. For example, the display may indicate textually which electrodes would be suitable for anode guard electrodes using, for example, an electrode number, lead number, position reference, or the like, or any combination thereof. In some embodiments, the display may indicate graphically on a graphical representation of the electrode arrangement, or any other suitable graphical representation, which electrodes would be suitable for anode guard electrodes.

Alternatively or additionally, the determination is provided to a control module or other programming unit for providing a stimulation regimen using the selected cathode(s). In at least some embodiments, the user or practitioner can override the determined anode guard electrodes and select one or more other electrodes (or a subset of the determined anode guard electrodes) for use as anode guard electrode(s).

FIG. 5 illustrates another method in which steps 502, 504, 506, and 508 are the same as steps 402, 404, 406, and 408, respectively. In step 510, the selected cathode(s) and determined anode guard electrode(s) are used to stimulate tissue by sending stimulation signals from a control module, or other signal source, to the appropriate electrodes.

In at least some embodiments, the determination of anode guard electrode(s) and their incorporation in an electrical stimulation program may be automatic when a user initiates the process. For example, the user may initiate the process by selecting a command. For example, the command might be labeled "focus" (due to the focusing nature of the anode guard electrodes) or "anode guard selection" or the like which initiates the process of FIG. 5. In at least some embodiments, the anode guard electrodes may be determined and incorporated into an electrical stimulation program without further user intervention. In at least some embodiments, the user may override or the user may be asked to confirm the determination of the anode guard electrodes prior to, or subsequent to, their incorporation into the electrical stimulation program. Any of the steps described herein with respect to FIGS. 4 and 5 may be performed using the control module, an external control module, or another computing device, or any combination thereof.

Figure 6:
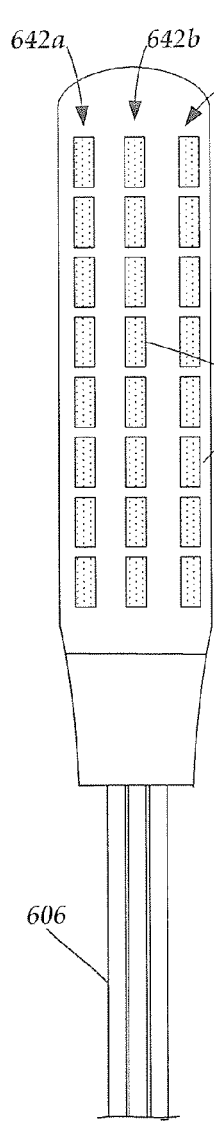
FIG. 6 is a schematic top view of one embodiment of a paddle for a paddle lead, according to the invention.

FIGS. 6-12 illustrates some lead configurations that can be used with the methods described above. In some embodiments, the electrodes are provided on one or more paddle leads. FIG. 6 illustrates a paddle 604 of a paddle lead with one or more lead bodies 606 extending from the paddle. The paddle 604 includes three columns 642a, 642b, 642c of electrodes 634 that are situated on the paddle so that they can be used to stimulate the spinal cord when the paddle lead is implanted near the spinal cord (for example, in the epidural space.)

Each of the columns 642a, 642b, 642c can include any number of electrodes 634 including, but not limited to, one, two, three, four, five, six, seven, eight, nine, ten, twelve, sixteen, or more electrodes. The electrodes 634 in each of the columns 642a, 642b, 642c can be spaced apart longitudinally in a uniform manner, as illustrated in FIG. 6, or in any other regular or irregular pattern. The electrodes 634 can be identical in size and shape or differ in size or shape. The columns 642a, 642b, 642c may have the same number of electrodes 634 or different numbers of electrodes. The columns 642a, 642b, 642c can be identical with respect to arrangement of the electrodes 634 or can be different. The electrodes of one column can be aligned with the electrodes of the other column or they can be unaligned or any combination thereof.

Any of the electrodes 634 (for example, electrode 634a) can be selected as a cathode. The guard anode electrodes can be mediolaterally (to the left or right in FIG. 6) disposed with respect to selected cathode 634a or rostrocaudally (to the top or bottom in FIG. 6) disposed with respect to the selected cathode 634a or any combination thereof (for example, diagonally disposed or one or more anode guards mediolaterally disposed and one or more anode guards rostrocaudally disposed.) These considerations apply to any of the electrode arrangements described herein.

Figure 7:
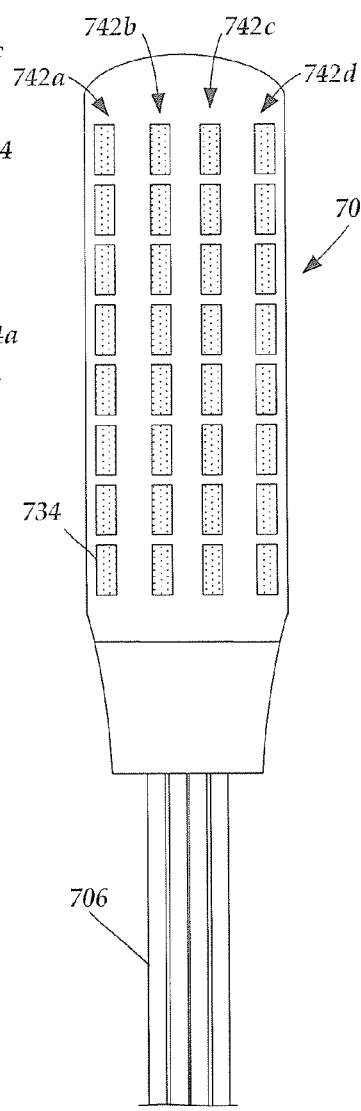
FIG. 7 is a schematic top view of a second embodiment of a paddle for a paddle lead, according to the invention.
Figure 8:
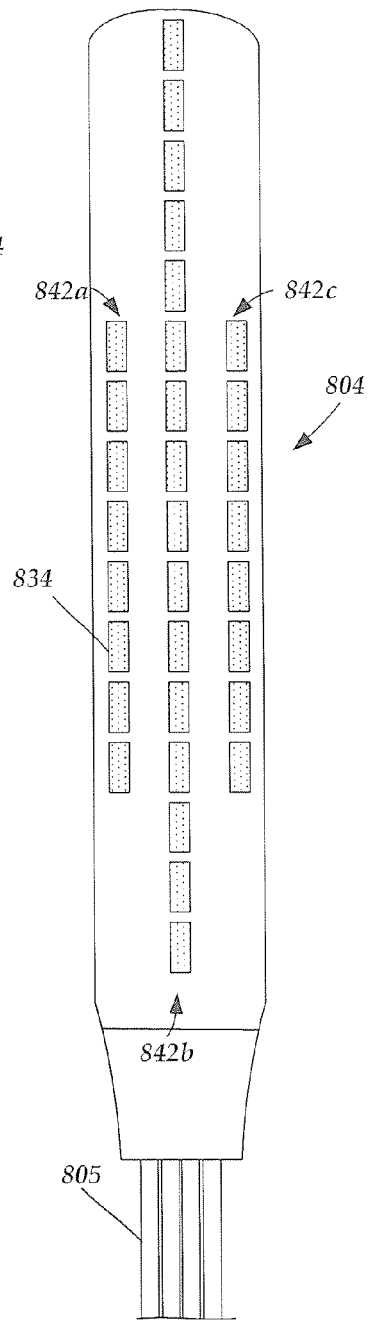
FIG. 8 is a schematic top view of a third embodiment of a paddle for a paddle lead, according to the invention.
Figure 9:
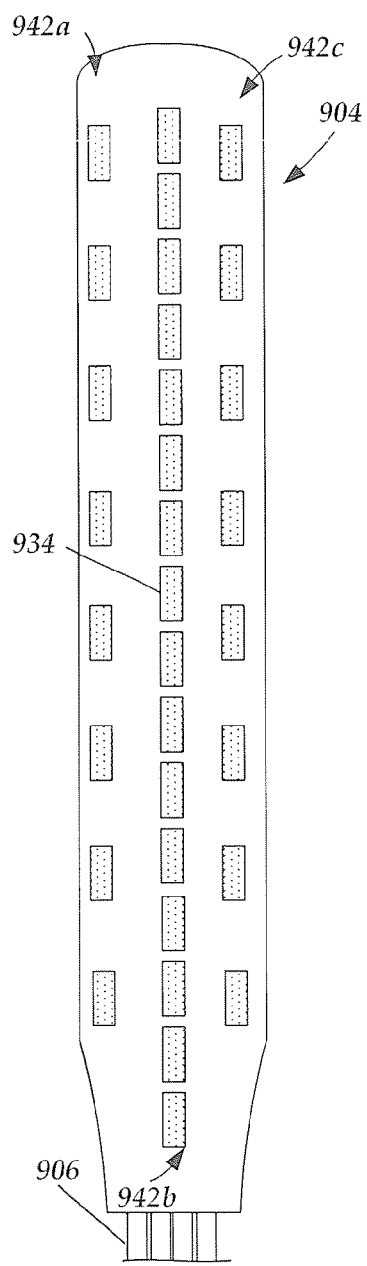
FIG. 9 is a schematic top view of a fourth embodiment of a paddle for a paddle lead, according to the invention.

The paddle 604 is illustrated in FIG. 6 has three columns, but it will be understood that such an arrangement can have any number of columns including, but not limited to, one, two, three, four, six, or more columns. For example, FIG. 7 illustrates a paddle 704 with four columns 742a, 742b, 742c, 742d of electrode 734 and one or more lead bodies 706. FIG. 8 illustrates a paddle 804 with three columns 842a, 842b, 842c of electrodes 834 and one or more lead bodies 806 where columns 842a, 842c have a different number and arrangement of electrodes than column 842b. FIG. 9 illustrates a paddle 904 with three columns 942a, 942b, 942c of electrodes 934 and one or more lead bodies 906 where columns 942a, 942c have a different number of electrodes and different spacing between electrodes than column 942b.

Figure 10:
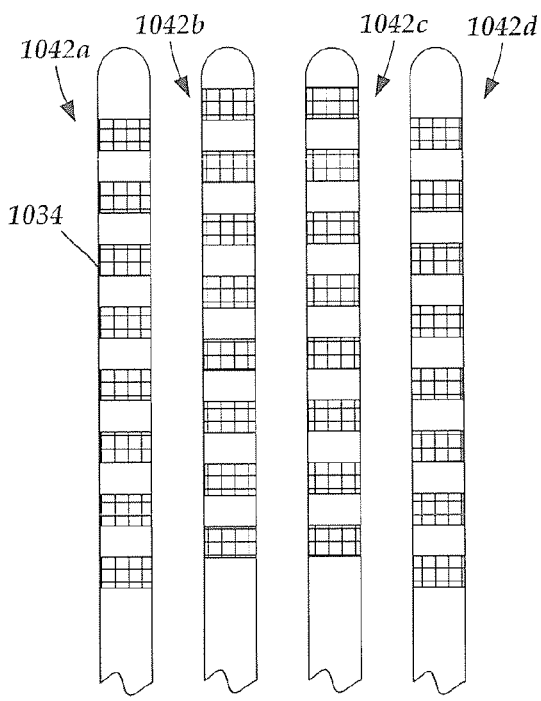
FIG. 10 is a schematic top view of one embodiment of an arrangement of the distal ends of four cylindrical lead bodies for electrical stimulation, according to the invention.

Alternatively, cylindrical or isodiametric lead bodies, such as those found in percutaneous leads, can be used instead of a paddle. Reference to "cylindrical" and "isodiametric" is directed to at least the distal end portion of the lead where the electrode reside and immediately proximal to the electrodes, but the cylindrical or isodiametric characteristic may, at least in some embodiments, extend the entire length of the lead (or at least the entire length of the lead excluding the portion where the terminals reside.) FIG. 10 illustrates four cylindrical lead bodies 1042a, 1042b, 1042c, and 1042d that are disposed in an arrangement similar to the arrangement of paddle 704 of FIG. 7. Those lead bodies 1042a, 1042b, 1042c, 1042d include ring electrodes 1034 and are implanted to stimulate the spinal cord. Further description of percutaneous leads with single or multiple lead bodies can be found at, for example, U.S. Pat. No. 8,332,049 and U.S. Patent Application Publications Nos. 2010/0070009; 2011/0009933; 2011/0029052; 2012/0215295; and 2012/0316610, all of which are incorporated herein by reference.

Figure 11:
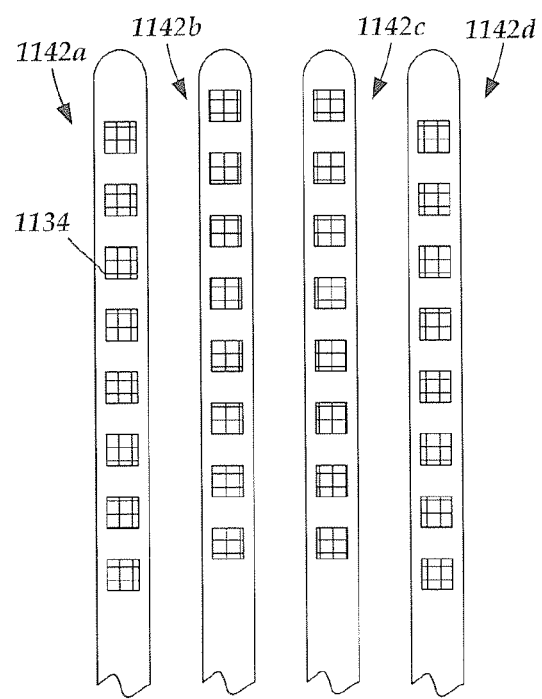
FIG. 11 is a schematic top view of a second embodiment of an arrangement of the distal ends of four cylindrical lead bodies for electrical stimulation, according to the invention.

FIG. 11 illustrates a similar arrangement of four cylindrical lead bodies 1142a, 1142b, 1142c, and 1142d. The electrodes 1134a on these lead bodies are segmented electrodes. Each segmented electrode extends only part way (e.g., no more than 75%, 67%, 60%, 50%, 40%, 33%, 25%, 20%, 17%, or 15% or less) around the circumference of the lead body. In some embodiments, there may be multiple segmented electrodes disposed around the circumference of the lead at each longitudinal position. Further description of segmented electrodes can be found at, for example, U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321, all of which are incorporated herein by reference. It will also be understood that the lead bodies may incorporate any combination of ring electrodes and segmented electrodes and may also incorporate at tip electrode at the end of the lead.

Although FIGS. 10 and 11 both illustrate using four lead bodies, it will be understood that other embodiments will include any number of lead bodies (including, but not limited to, zero, one, two, three, four, six, or more lead bodies) for spinal cord stimulation. The electrodes of the lead bodies may be aligned or not aligned. One possible advantage of the arrangements in FIGS. 10 and 11 is that, at least in some embodiments, the lead bodies can be percutaneously implanted individually using an introducer. Paddle leads are often surgically implanted.

Figure 12:
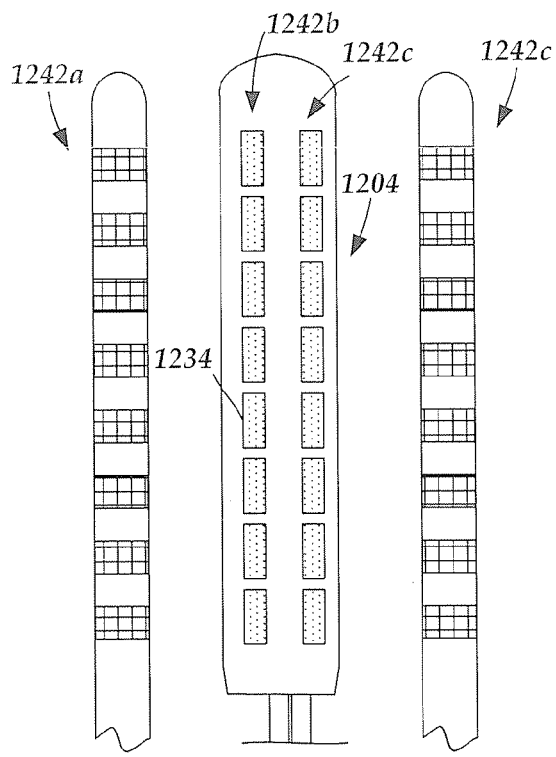
FIG. 12 is a schematic top view of one embodiment of an arrangement of the distal ends of two cylindrical lead bodies and a paddle of a paddle lead for electrical stimulation, according to the invention.

Some embodiments can combine cylindrical leads with paddle leads. FIG. 12 illustrates an embodiment that includes both cylindrical leads 1242a, 1242d and a paddle 1204 with two columns 1242b, 1242c of electrodes 1234. Any number of cylindrical leads (for example, one, two, three, four, five, six, eight, or more leads) and any number of paddle leads (for example, one, two, three, four, or more leads) can be used together. FIGS. 10-12 illustrates the leads arranged side by side, but it will be recognized that two or more of the leads could also be arranged longitudinally along the spinal cord instead of laterally.

FIG. 13 is a schematic overview of one embodiment of components of an electrical stimulation system 1300 including an electronic subassembly 1310 disposed within a control module. It will be understood that the electrical stimulation system can include more, fewer, or different components and can have a variety of different configurations including those configurations disclosed in the stimulator references cited herein.

Some of the components (for example, a power source 1312, an antenna 1318, a receiver 1302, and a processor 1304) of the electrical stimulation system can be positioned on one or more circuit boards or similar carriers within a sealed housing of an implantable pulse generator, if desired. Any power source 1312 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1318 or a secondary antenna. The external power source can be in a device that is mounted on the skin of the user or in a unit that is provided near the user on a permanent or periodic basis.

If the power source 1312 is a rechargeable battery, the battery may be recharged using the optional antenna 1318, if desired. Power can be provided to the battery for recharging by inductively coupling the battery through the antenna to a recharging unit 1316 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 1304 is generally included to control the timing and electrical characteristics of the electrical stimulation system. For example, the processor 1304 can, if desired, control one or more of the timing, frequency, strength, duration, and waveform of the pulses. In addition, the processor 1304 can select which electrodes can be used to provide stimulation, if desired. In some embodiments, the processor 1304 selects which electrode(s) are cathodes and which electrode(s) are anodes. In some embodiments, the processor 1304 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1308 that, for example, allows modification of pulse characteristics. In the illustrated embodiment, the processor 1304 is coupled to a receiver 1302 which, in turn, is coupled to the optional antenna 1318. This allows the processor 1304 to receive instructions from an external source to, for example, direct the pulse characteristics and the selection of electrodes, if desired.

In one embodiment, the antenna 1318 is capable of receiving signals (e.g., RF signals) from an external telemetry unit 1306 which is programmed by the programming unit 1308. The programming unit 1308 can be external to, or part of, the telemetry unit 1306. The telemetry unit 1306 can be a device that is worn on the skin of the user or can be carried by the user and can have a form similar to a pager, cellular phone, or remote control, if desired. As another alternative, the telemetry unit 1306 may not be worn or carried by the user but may only be available at a home station or at a clinician's office. The programming unit 1308 can be any unit that can provide information to the telemetry unit 1306 for transmission to the electrical stimulation system 1300. The programming unit 1308 can be part of the telemetry unit 1306 or can provide signals or information to the telemetry unit 1306 via a wireless or wired connection. One example of a suitable programming unit is a computer operated by the user or clinician to send signals to the telemetry unit 1306.

The signals sent to the processor 1304 via the antenna 1318 and the receiver 1302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1300 to cease operation, to start operation, to start charging the battery, or to stop charging the battery. In other embodiments, the stimulation system does not include the antenna 1318 or receiver 1302 and the processor 1304 operates as programmed.

Optionally, the electrical stimulation system 1300 may include a transmitter (not shown) coupled to the processor 1304 and the antenna 1318 for transmitting signals back to the telemetry unit 1306 or another unit capable of receiving the signals. For example, the electrical stimulation system 1300 may transmit signals indicating whether the electrical stimulation system 1300 is operating properly or not or indicating when the battery needs to be charged or the level of charge remaining in the battery. The processor 1304 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of stimulating a portion of a spinal cord of a patient, the method comprising:
   identifying an arrangement of a plurality of electrodes including a relative placement of each electrode within the arrangement;

identifying a vertebral level for implantation of the arrangement and a position of the arrangement with respect to the spinal cord;

determining by calculation, for a selection of a cathode from the plurality of electrodes, at least two anode guard electrodes from the plurality of electrodes including in the calculation an estimated thickness of cerebrospinal fluid at the vertebral level, wherein, in the calculation, a distance between each anode guard electrode and the cathode is inversely related to the estimated thickness of cerebrospinal fluid at the vertebral level; and stimulating the portion of the spinal cord of the patient at the vertebral level using the cathode and the at least two anode guard electrodes.

2. The method of claim 1, further comprising, after determining the at least two anode guard electrodes, displaying an indication of the at least two anode guard electrodes for view by an operator.

3. The method of claim 2, wherein displaying an indication comprises displaying a schematic representation of the arrangement with an indication of which electrodes of the arrangement correspond to the at least two anode guard electrodes.

4. The method of claim 1, further comprising implanting one or more leads to form the arrangement of the plurality of electrodes.

5. The method of claim 4, wherein implanting one or more leads comprises implanting at least one paddle lead with the arrangement of the plurality of electrodes disposed thereon.

6. The method of claim 4, wherein implanting one or more leads comprises implanting at least two cylindrical leads to form the arrangement of the plurality of electrodes.

7. The method of claim 4, wherein implanting one or more leads comprises implanting at least one paddle lead and at least one cylindrical lead to form the arrangement of the plurality of electrodes disposed thereon.

8. A method of identifying a selection of electrodes for stimulating a portion of a spinal cord of a patient, the method comprising:

identifying an arrangement of a plurality of electrodes including a relative placement of each electrode within the arrangement;

identifying a vertebral level for implantation of the arrangement and a position of the arrangement with respect to the spinal cord;

determining by calculation, for a selection of a cathode from the plurality of electrodes, at least two anode guard electrodes from the plurality of electrodes including in the calculation an estimated thickness of cerebrospinal fluid at the vertebral level, wherein, in the calculation, a distance between each anode guard electrode and the cathode is inversely related to the estimated thickness of cerebrospinal fluid at the vertebral level;

displaying an indication of the at least two anode guard electrodes for view by a practitioner; and transmitting to a control module of an electrical stimulation system the selection of the cathode and the determined at least two anode guard electrodes to initiate stimulation of a patient using the cathode and at least two anode guard electrodes.

9. The method of claim 8, further comprising implanting one or more leads to form the arrangement of the plurality of electrodes.

10. The method of claim 9, wherein implanting one or more leads comprises implanting at least one paddle lead with the arrangement of the plurality of electrodes disposed thereon.

11. The method of claim 9, wherein implanting one or more leads comprises implanting at least two cylindrical leads to form the arrangement of the plurality of electrodes.

12. The method of claim 9, wherein implanting one or more leads comprises implanting at least one paddle lead and at least one cylindrical lead to form the arrangement of the plurality of electrodes disposed thereon.

13. A non-transitory computer-readable storage medium having processor-executable instructions, the processor-executable instructions when installed onto a system enable the system to perform actions, comprising:

receiving an indication of an arrangement of a plurality of electrodes including a relative placement of each electrode within the arrangement;

receiving a vertebral level for implantation of the arrangement and a position of the arrangement with respect to the spinal cord;

determining by calculation, for a selection of a cathode from the plurality of electrodes, at least two anode guard electrodes from the plurality of electrodes including in the calculation an estimated thickness of cerebrospinal fluid at the vertebral level, wherein, in the calculation, a distance between each anode guard electrode and the cathode is inversely related to the estimated thickness of cerebrospinal fluid at the vertebral level;

displaying an indication of the at least two anode guard electrodes; and transmitting to a control module of an electrical stimulation system the selection of the cathode and the determined at least two anode guard electrodes to initiate stimulation of a patient using the cathode and at least two anode guard electrodes.

14. The non-transitory computer-readable storage medium of claim 13, wherein the processor-executable instructions further comprise receiving an indication of whether the anode guard electrodes are to be mediolateral or rostrocaudal or a combination thereof with respect to the cathode.

15. A system for determining electrodes for use in electrical stimulation, the system comprising:

a display; and at least one processor coupled to the display, the at least one processor is configured and arranged to receive an indication of an arrangement of a plurality of electrodes including a including relative placement of each electrode within the arrangement;

receive a vertebral level for implantation of the arrangement and a position of the arrangement with respect to the spinal cord;

determine by calculation, for a selection of a cathode from the plurality of electrodes, at least two anode guard electrodes from the plurality of electrodes including in the calculation an estimated thickness of cerebrospinal fluid at the vertebral level, wherein, in the calculation, a distance between each anode guard electrode and the cathode is inversely related to the estimated thickness of cerebrospinal fluid at the vertebral level;

display on the display an indication of the at least two anode guard electrodes; and transmit to a control module of an electrical stimulation system the selection of the cathode and the determined at least two anode guard electrodes to initiate stimulation of a patient using the cathode and at least two anode guard electrodes.

16. The system of claim 15, further comprising the control module configured and arranged to receive at least one implantable electrical stimulation lead.

17. The system of claim 16, wherein the control module comprises at least one of the at least one processor.

18. The system of claim 16, further comprising at least one lead configured and arranged for coupling to the control module.

19. The system of claim 15, wherein the at least one processor is also configured and arranged to receive an indication of whether the anode guard electrodes are to be mediolateral or rostrocaudal or a combination thereof with respect to the cathode.

* * * * *